(12) United States Patent
Abbott-Banner et al.

(10) Patent No.: US 11,759,467 B2
(45) Date of Patent: *Sep. 19, 2023

(54) TREATMENT

(71) Applicant: VERONA PHARMA PLC, Cardiff (GB)

(72) Inventors: Katharine Abbott-Banner, London (GB); John Hanrahan, Montreal (CA); David Thomas, Montreal (CA)

(73) Assignee: VERONA PHARMA PLC, Cardiff (GB)

( * ) Notice: Subject to any disclaimer, the term of this patent is extended or adjusted under 35 U.S.C. 154(b) by 224 days.

This patent is subject to a terminal disclaimer.

(21) Appl. No.: 17/099,598

(22) Filed: Nov. 16, 2020

(65) Prior Publication Data

US 2021/0106585 A1 Apr. 15, 2021

Related U.S. Application Data

(62) Division of application No. 15/310,693, filed as application No. PCT/GB2015/051377 on May 11, 2015, now Pat. No. 10,864,213.

(30) Foreign Application Priority Data

May 12, 2014 (GB) .................................... 1408384
Oct. 7, 2014 (GB) .................................... 1417719

(51) Int. Cl.
| | | |
|---|---|---|
| *A61K 31/519* | (2006.01) | |
| *A61K 31/404* | (2006.01) | |
| *A61K 31/443* | (2006.01) | |
| *A61K 31/47* | (2006.01) | |
| *A61K 45/06* | (2006.01) | |

(52) U.S. Cl.
CPC .......... *A61K 31/519* (2013.01); *A61K 31/404* (2013.01); *A61K 31/443* (2013.01); *A61K 31/47* (2013.01); *A61K 45/06* (2013.01)

(58) Field of Classification Search
CPC .. A61K 31/519; A61K 31/404; A61K 31/443; A61K 31/47; A61K 45/06
USPC ........................................................ 514/267
See application file for complete search history.

(56) References Cited

U.S. PATENT DOCUMENTS

| | | | |
|---|---|---|---|
| 5,225,193 A | 7/1993 | Bartfai | |
| 5,874,063 A | 2/1999 | Briggner et al. | |
| 5,983,956 A | 11/1999 | Trofast | |
| 6,221,398 B1 | 4/2001 | Jakupovic et al. | |
| 6,268,533 B1 | 7/2001 | Gao et al. | |
| 6,475,524 B1 | 11/2002 | Bizrat et al. | |
| 6,613,307 B1 | 9/2003 | Cooper | |
| 6,794,391 B2 | 9/2004 | Oxford et al. | |
| 7,105,663 B2 | 9/2006 | Oxford et al. | |
| 7,378,424 B2 | 5/2008 | Oxford et al. | |
| 8,242,127 B2 | 8/2012 | Oxford et al. | |
| 9,062,047 B2 | 6/2015 | Walker et al. | |
| 9,700,558 B2 | 7/2017 | Walker et al. | |
| 9,717,732 B2 | 8/2017 | Walker et al. | |
| 9,956,171 B2 | 5/2018 | Spargo et al. | |
| 10,463,665 B2 | 11/2019 | Spargo et al. | |
| 10,471,063 B2 | 11/2019 | Walker et al. | |
| 10,710,998 B2 | 7/2020 | Spargo | |
| 10,864,213 B2 | 12/2020 | Abbott-Banner et al. | |
| 10,945,950 B2 | 3/2021 | Spargo et al. | |
| 11,491,155 B2 | 11/2022 | Spargo et al. | |
| 2003/0036542 A1 | 2/2003 | Oxford et al. | |
| 2004/0171828 A1 | 9/2004 | Oxford et al. | |
| 2004/0176353 A1 | 9/2004 | Oxford et al. | |

(Continued)

FOREIGN PATENT DOCUMENTS

| | | |
|---|---|---|
| EP | 0 717 987 | 6/1996 |
| EP | 2 489 659 | 8/2012 |

(Continued)

OTHER PUBLICATIONS

Condren et al J. Pediatr Pharmacol Ther, 2013, 18(1), 9-13 (Year: 2013).*
Davies et al BMJ, 2007, 335 1255-1259 (Year: 2007).*
Assessment report European Medicines Agency, Committee for Medicinal products for human use, 2012 (Year: 2012).*
Au et al., Br J Pharmacol. (1998) 123(6): 1260-6.

(Continued)

*Primary Examiner* — Yevgeny Valenrod
(74) *Attorney, Agent, or Firm* — Kilpatrick Townsend & Stockton LLP

(57) ABSTRACT

The invention provides a compound for use in treating or preventing a disease or condition selected from cystic fibrosis, chronic obstructive pulmonary disease (COPD), asthma, mild pulmonary disease, bronchitis, bronchiectasis, idiopathic bronchiectasis, allergic bronchopulmonary aspergillosis, sinusitis, rhinosinusitis, CFTR-related metabolic syndrome (CRMS), pancreatitis, idiopathic chronic pancreatitis and Sjörgren's syndrome, or for use in preventing male infertility caused by congenital absence of the vas deferens, in a patient by modulating CFTR activity, which compound is 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof. The invention also provides a composition comprising (i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof and (ii) a leukotriene receptor antagonist. The invention also provides a composition comprising (i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof and (ii) a CFTR potentiator or a CFTR corrector.

14 Claims, 12 Drawing Sheets

(56) References Cited

U.S. PATENT DOCUMENTS

| | | |
|---|---|---|
| 2008/0206163 A1 | 8/2008 | Oxford et al. |
| 2011/0065678 A1 | 3/2011 | Armani et al. |
| 2012/0134934 A1 | 5/2012 | Armani et al. |
| 2012/0302533 A1 | 11/2012 | Oxford et al. |
| 2013/0045988 A1 | 2/2013 | Lefebvre et al. |
| 2013/0224293 A1 | 8/2013 | Dokou et al. |
| 2013/0225616 A1 | 8/2013 | Walker et al. |
| 2016/0000790 A1 | 1/2016 | Walker et al. |
| 2016/0008363 A1 | 1/2016 | Walker et al. |
| 2017/0112839 A1 | 4/2017 | Abbott-Banner et al. |
| 2017/0239178 A1 | 8/2017 | Spargo et al. |
| 2017/0266190 A1 | 9/2017 | Walker et al. |
| 2018/0021337 A1 | 1/2018 | Spargo et al. |
| 2018/0369139 A1 | 12/2018 | Spargo et al. |
| 2019/0330206 A1 | 10/2019 | Spargo |
| 2020/0016158 A1 | 1/2020 | Spargo et al. |
| 2021/0379053 A1 | 12/2021 | Spargo et al. |
| 2023/0112220 A1 | 4/2023 | Spargo et al. |

FOREIGN PATENT DOCUMENTS

| | | | |
|---|---|---|---|
| RU | 2512682 C2 | 4/2014 | |
| WO | 1992/022286 | 12/1992 | |
| WO | 1999/053901 | 10/1999 | |
| WO | 2000/058308 | 10/2000 | |
| WO | 2000/061108 | 10/2000 | |
| WO | 2009/112274 | 9/2009 | |
| WO | 2010/053471 A1 | 5/2010 | |
| WO | 2012/020016 | 2/2012 | |
| WO | WO-2012020016 A1 * | 2/2012 | ........... A61K 31/519 |
| WO | 2012/107364 A1 | 8/2012 | |
| WO | 2014/140647 | 3/2014 | |
| WO | 2014/140648 | 3/2014 | |

OTHER PUBLICATIONS

Balghi et al., FASEB J (2011) 25, 4274-4291.
Banner et al., J Cyst Fibros. (2009) 8(1):1-8.
Baroni et al., "Direct interaction of a CFTR potentiator and a CFTR corrector with phospholipid bilayers," Eur Biophys J, Published online Apr. 26, 2014; 7 pages.
Bielekova et al. (2000), J Immunol. 164(2):1117-24.
Billet et al., The Journal of Physiology (2013) 591(21): 5273-5278.
Blanchard et al. (2014) The FASEB Journal 28(2) 791-801.
Bonfeld et al., Am J Respir Crit Care Med (1995) 152, 2111-2118.
Calzetta et al., Journal of Pharmacology and Experimental Therapeutics, Sep. 2013, 34(3) 414-423.
Cervin (1998) Aurus, Nasus, Larynx 25(3): 269-276.
Chappe et al., British Journal of Pharmacology, (1998), 123:683-693.
Char et al., "A Little CFTR Goes a Long Way: CFTR-Dependent Sweat Secretion from G551D and R117H-5T Cystic Fibrosis Subjects Taking Ivacaftor," PLOS ONE 9(2): e88564; 16 pages. https://doi.org/10.1371/journal.pone.0088564.
Cobb et al. (2003) Am. J. Respir. Cell Mol. Biol., 29, 410-418.
Conway et al., "A pilot study of zafirlukast as an anti-inflammatory agent in the treatment of adults with cystic fibrosis," Journal of Cystic Fibrosis 2 (2003) 25-28.
Franciosi et al., The Lancet, Respiratory Medicine (2013) 1(9): 714-727.
Giembycz et al. (1996) Br J Pharmacol 118: 1945-1958.
Grahame-Smith et al., Oxford Handbook of Clinical Pharmacology and Pharmacotherapy, M., Medicine 2000, parts 10 and 10.1; 3 pages.
Haddad et al. (2002) J Pharmacol Exp Ther 300: 559-566.
Hunter, MJ et al. (2010) PLOS One (2010) 5. e11598.
International Search Report; PCT Application No. PCT/GB2015/051377; dated Jul. 23, 2015, 2 pages.
Jones et al. (2005) Pulm Pharmacol Ther 18(2):93-101.
Kelley et al. (1995) Am. J. Respir. Cell Mol. Biol., 13(6), 657-664.
Kubo et al. (2012) Int Immunopharmacol, 12(1):59-63.
Lambert et al. (2014) Am J. Repir Cell Mol Biol. 50(3):549-58.
Leier et al., "Sildenafil Acts as Potentiator and Corrector of CFTR but Might be not Suitable for the Treatment of CF Lung Disease," Cell Physiol Biochem 2012; 29:775-790.
Liu et al., JPET, (2005), 314:846-854.
Matthes et al., Pediatric Pulmonology, (2015) 49(sup. 038) 277.
Moss et al. (2013) J Cystic Fibros. 12(3): 241-8.
Murphy et al., Journal of Heart and Lung transplantation. (2006), 25: 1436-1440.
Noone and Knowles (2001) Respiratory Research 2(6): 328-32.
Pathomthongtaweechai et al., "Pranlukast inhibits renal epithelial cyst progression via activation of AMP-activated protein kinase," European Journal of Pharmacology, 724 (2014) 67-76.
Rennard et al., Drugs, (2008) 68 (Suppl 2), 3-57.
Rowe et al., "Cystic Fibrosis Transmembrane Regulator Correctors and Potentiators," Cold Spring Harb Perspect Med 2013, 3:a009761; 15 pages.
Shan et al. (2012) J Physiol, 590, 5273-5297.
Smith et al., Am J Respir. Cell Mol. Biol. (1999), 20:129-134.
Sousa et al., J Leukoc Biol.; May 2010, 87(5):895-904.
Tabcharani et al. (1991) Nature 352, 628-631.
Turner, Mark J. et al., "The dual phosphodiesterase 3 and 4 inhibitor RPL554 stimulates CFTR and ciliary beating in primary cultures of bronchial epithelia," Am J Physiol Lung Cell Mol Physiol 310: L59-L70, 2016.
Turner, Mark J. et al., "The dual phosphodiesterase 3/4 inhibitor RPL554 stimulates rare class III and IV CFTR mutants," Am J Physiol Lung Cell Mol Physiol 318: L908-L920, 2020.
UK Cystic Fibrosis Registry Annual Data report 2013: Summary Jul. 2014, 33 pages, available from https://www.cysticfibrosis.org.uk/the-work-we-do/uk-cf-registry/reporting-and-resources.
Veit et al. (2012). Mol Biol Cell 23, 4188-4202.
Wright et al. (1998) The American journal of physiology, 275, L694-700.
Zhao et al., "MRP transporters as membrane machinery in the bradykinin-inducible export of ATP," Naunyn-Schmied Arch Pharmacol (2010) 381:315-320.
Mogayzel, Peter J., Jr. et al., "Cystic Fibrosis Pulmonary Guidelines," American Journal of Respiratory and Critical Care Medicine, 2013, 187, 680-689.

* cited by examiner

TREATMENT

CROSS-REFERENCES TO RELATED APPLICATIONS

This application is a divisional of U.S. patent application Ser. No. 15/310,693, filed Nov. 11, 2016, which is a National Phase Entry of International Patent Application No. PCT/GB2015/051377, filed May 11, 2015, which claims priority to United Kingdom Patent Application No. 1408384.4, filed May 12, 2014, and United Kingdom Patent Application No. 1417719.0, filed Oct. 7, 2014, the teachings of which are incorporated herein by reference in their entireties for all purposes.

FIELD OF THE INVENTION

The present invention relates to the treatment of disorders associated with the activity of cystic fibrosis transmembrane conductance regulator (CFTR), for instance cystic fibrosis (CF).

BACKGROUND OF THE INVENTION

CFTR controls transmembrane conductance and Cl-secretion in epithelial cells. It thus controls the movement of fluids across membranes. Deficient CFTR activity can lead to insufficient fluids in the airways or other organs, which is undesirable.

Several diseases are associated with malfunctions of CFTR, most importantly cystic fibrosis. Cystic fibrosis is the most common fatal genetic disorder in humans of European inheritance, and it is estimated that between 1 in 2000 and 1 in 3000 newborns in the European Union are affected by CF.

RPL554 (9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one) is a dual PDE3/PDE4 inhibitor and is described in WO 00/58308. As a combined PDE3/PDE4 inhibitor, RPL554 is known to have both anti-inflammatory and bronchodilator activity. WO 00/58308 suggests the use of a number of compounds, including RPL554, as anti-inflammatory drugs to treat the symptoms of a number of diseases, including CF.

Although anti-inflammatory drugs are often useful in treating the symptoms of some conditions mediated by CFTR malfunction, there remains a medical need for treatments that are able to address the underlying etiology of such conditions, by modulating the activity of CFTR. In this regard, a number of disease-modifying cystic fibrosis drugs are under development. An example is ivacaftor (VX770), which is disclosed in WO 2011/0722241.

Disease-modifying cystic fibrosis drugs are a different drug category to anti-inflammatories. Further, PDE3/PDE4 inhibition is not necessarily associated with successful activation of CFTR. For example the PDE4 (phosphodiesterase 4) inhibitor roflumilast was found to have no effect on Cl-secretion in T84 human colonic cells (Liu et al., JPET, (2005), 314:846-854). No effect on Cl-secretion has been observed for milrinone (a PDE 3 inhibitor) following nasal administration to subjects with wild type (WT) CFTR, CFTR with the ΔF508 mutation, or CFTR with the G551D mutation (Smith et al., Am. J. Respir. Cell Mol. Biol. (1999), 20:129-134). Rolipram and Ro 20-1724 (both PDE 4 inhibitors) were found to have no effect on WT CFTR in CHO cells (Chappe et al., British Journal of Pharmacology, (1998), 123:683-693).

Where drugs are found to activate CFTR, they often cause diarrhoea as a side effect that results from increased transport of fluids into the colon.

SUMMARY OF THE INVENTION

It is a surprising finding of the present invention that RPL554 is active in modulating CFTR activity. RPL554 has been found to activate CFTR in primary human bronchial epithelial cells and also CFBE (immortalised CF human bronchial epithelial cell line) monolayers stably expressing WT CFTR. Furthermore, RPL554 does not have the side effect of diarrhoea commonly associated with other drugs active at CFTR.

It is also a finding of the invention that RPL554 can interact synergistically with leukotriene receptor antagonists to activate CFTR, increasing Cl-current.

RPL554 is therefore active as a disease modifying agent for treating cystic fibrosis, and other diseases mediated by CFTR malfunction.

Accordingly, the present invention provides a compound for use in treating or preventing a disease or condition selected from cystic fibrosis, chronic obstructive pulmonary disease (COPD), asthma, mild pulmonary disease, bronchitis, bronchiectasis, idiopathic bronchiectasis, allergic bronchopulmonary aspergillosis, sinusitis, rhinosinusitis, CFTR-related metabolic syndrome (CRMS), pancreatitis, idiopathic chronic pancreatitis and Sjörgren's syndrome, or for use in preventing male infertility caused by congenital absence of the vas deferens, in a patient by modulating CFTR activity, which compound is 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof. Preferably, the compound is for use as described herein in treating or preventing cystic fibrosis by modulating CFTR activity.

Patients with cystic fibrosis have deficient fluid transfer to the airways, which leads to viscous mucous, which is undesirable. The present invention therefore also provides a compound for use in increasing mucous mobility and/or reducing mucous viscosity, or for use in facilitating mucous membrane clearance from the airways, in a patient suffering from cystic fibrosis, which compound is 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof.

The invention also provides a composition comprising (i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof and (ii) a leukotriene receptor antagonist.

The invention also provides a composition comprising (i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof and (ii) a CFTR potentiator or a CFTR corrector.

DETAILED DESCRIPTION OF THE INVENTION

RPL554

Figure 1:
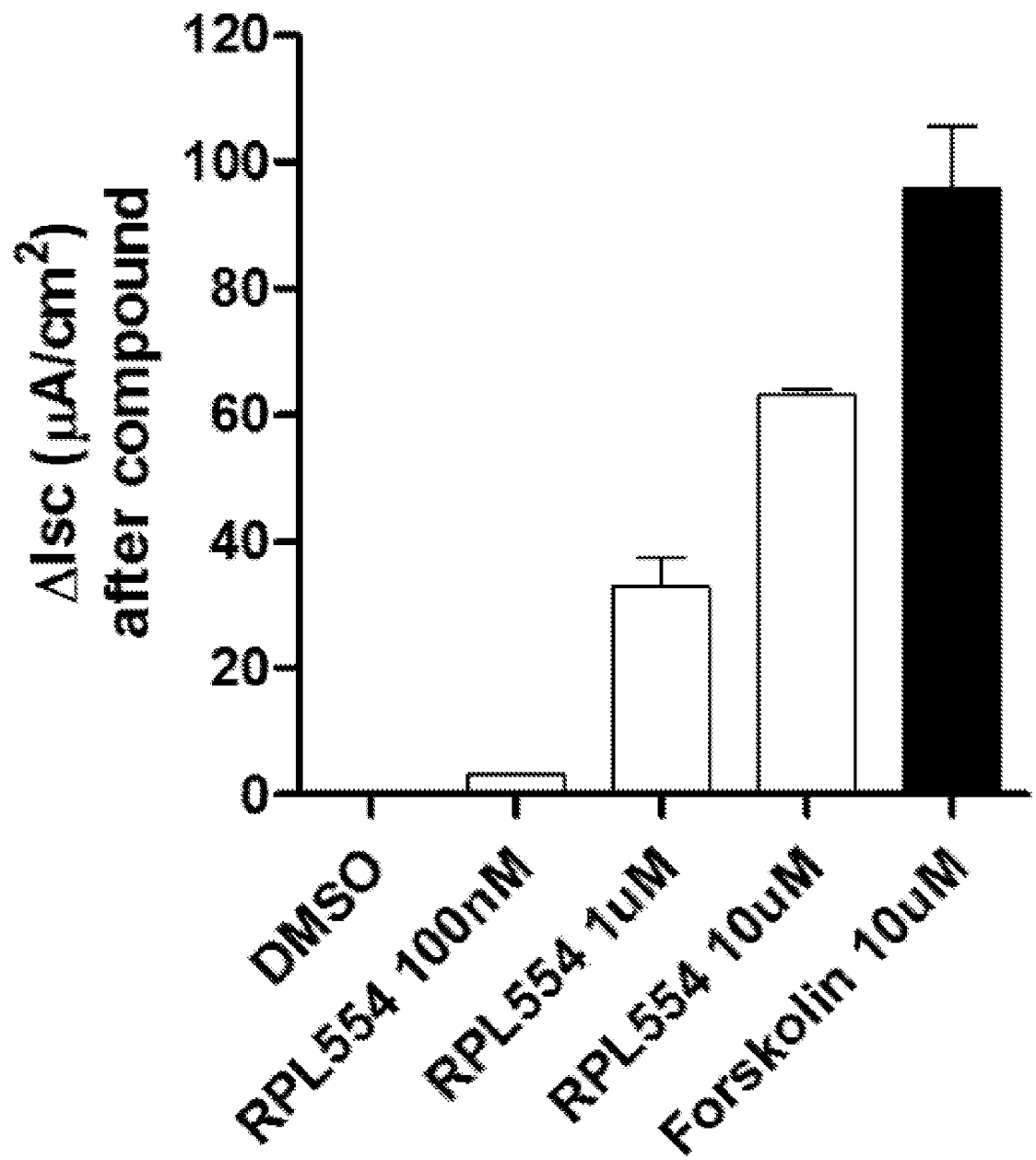
FIG. 1 shows the results of tests for activation of wild type (WT) CFTR in cystic fibrosis bronchial epithelial (CFBE) cell monolayers in Ussing chambers by RPL554 and forskolin.

9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one may be referred to as RPL554. RPL554 has the following structure:

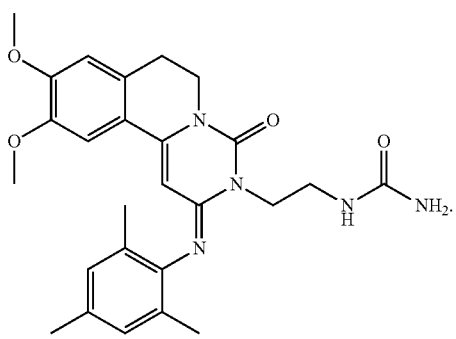 [SMILES: COc1cc2c(cc1OC)-c1c/c(=N\c3c(C)cc(C)cc3C)n(CCNC(N)=O)c(=O)n1CC2]

Systematic names for RPL554 include 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one and N-{2-[(2E)-2-(mesitylimino)-9,10-dimethoxy-4-oxo-6,7-dihydro-2H-pyrimido[6,1-a]-isoquinolin-3(4H)-yl]ethyl}urea.

The compound used in the treatment of the invention may be RPL554 or a pharmaceutically acceptable acid addition salt thereof. A pharmaceutically acceptable acid addition salt is a salt with a pharmaceutically acceptable acid.

For the avoidance of doubt, RPL5545 can, if desired, be used in the form of a solvate. Further, for the avoidance of doubt, the RPL554 may be used in any tautomeric form.

Diseases and Conditions

RPL554 can activate, potentiate and enhance CFTR. RPL554 can therefore treat diseases and conditions by modulating CFTR activity. CFTR is expressed in a number of cell types and particularly in epithelial cells. A function of CFTR is to provide a chloride channel across the membrane of cells that produce mucus, sweat, saliva and tears. These channels are vital for the function of several organs, including the lungs, pancreas and digestive system. Many diseases and conditions are associated with the function of CFTR. In particular, this includes cystic fibrosis, pancreatic disorders (for instance, idiopathic pancreatitis) and male infertility caused by congenital absence of the vas deferens.

Activity of the CFTR protein has been associated with problems affecting the digestive and respiratory systems in addition to those conditions described above. Typically, RPL554 may be used to treat conditions associated with CFTR function by modulating CFTR activity. Such conditions are well known.

Diseases or conditions which may be treated or prevented are typically selected from cystic fibrosis, chronic obstructive pulmonary disease (COPD), asthma, mild pulmonary disease, bronchitis, bronchiectasis, idiopathic bronchiectasis, allergic bronchopulmonary aspergillosis, sinusitis, rhinosinusitis, CFTR-related metabolic syndrome (CRMS), pancreatitis, idiopathic chronic pancreatitis and Sjörgren's syndrome, or the disease or condition which may be prevented is male infertility caused by congenital absence of the vas deferens. For instance, the disease or condition may be cystic fibrosis, chronic obstructive pulmonary disease (COPD), mild asthma, severe asthma, mild pulmonary disease, chronic bronchitis, chronic bronchiectasis, idiopathic chronic bronchiectasis, allergic bronchopulmonary aspergillosis, chronic sinusitis, chronic rhinosinusitis, CFTR-related metabolic syndrome (CRMS), acute pancreatitis, chronic pancreatitis, idiopathic acute pancreatitis, idiopathic chronic pancreatitis, Sjörgren's syndrome or male infertility caused by congenital absence of the vas deferens.

Preferably, the disease or condition is cystic fibrosis, chronic obstructive pulmonary disease (COPD), bronchitis, bronchiectasis, idiopathic bronchiectasis, allergic bronchopulmonary aspergillosis, sinusitis, rhinosinusitis, CFTR-related metabolic syndrome (CRMS), pancreatitis or idiopathic chronic pancreatitis. More preferably, the disease of condition is cystic fibrosis, chronic obstructive pulmonary disease (COPD), allergic bronchopulmonary aspergillosis, sinusitis, rhinosinusitis, CFTR-related metabolic syndrome (CRMS) or idiopathic chronic pancreatitis. Most preferably the disease or condition is cystic fibrosis.

In a preferred embodiment, the invention provides RPL554 for use in treating or preventing cystic fibrosis by modulating CFTR activity, in particular for use in treating cystic fibrosis by modulating CFTR.

Preferably, modulating CFTR activity comprises activating CFTR, potentiating CFTR or enhancing CFTR. More preferably, modulating CFTR activity comprises activating CFTR.

The compound may be for use in increasing mucous mobility or reducing mucous viscosity, in a patient suffering from cystic fibrosis. The compound may be for use in facilitating mucous membrane clearance from the airways, in a patient suffering from cystic fibrosis.

Patients

RPL554 can modulate activity of wild type CFTR or mutant CFTR. Typically, the patient has a CFTR mutation. A large number of CFTR mutations have been detected in individuals suffering from CF and other CFTR-related disorders. Examples of common mutations include F508del (ΔF508), G542X, G551D, N1303K, W1282X, R117H, R553X, P537H, G85E, 1717-1G→A, 621+1G→T, 2789+5G→A, 3849+10kbC→T, R1162X, G85E, 3120+1G→A, I507del (ΔI507), 1898+1G→A, 1898+5G→T, 3659delC, R347P, R560T, R334W, A455E, 2184delA, 3898insC, 3120+1kbdel8.6 kb, and 711+1G→T. Such mutations may be classed by their effect. There are 6 classes of CFTR mutations. Typically the CFTR mutation is a class III or class IV mutation. For instance the mutation may be a gating mutation. A gating mutation is a mutation which decreases the opening of the channel in CFTR proteins in the membrane. The CFTR mutation may be ΔF508, R117H, G542X, G551D, N1303K or W1282X. Preferably, the CFTR mutation is ΔF508, R117H or G551D, for instance ΔF508. For example, the patient may have the ΔF508 mutation or the R117H mutation, or both the ΔF508 and R117H mutations.

RPL554 has been shown to be particularly effective at modulating the R117H mutation in CFTR which causes conductance and gating abnormalities. CFTR mutations that cause defects in gating may be classified as class III mutations Examples of class III mutations include G551D, G178R, G551S, S549N and G1349D. CFTR mutations that result in defects in conductance are classified as class IV mutations. Examples of class IV mutations include R117H, R347P, R17C and R334W. Thus, the patient may have a CFTR mutation selected from G551D, G178R, G551S, S549N, G1349D, R117H, R117C, R347P and R334W. These are examples of CFTR gating mutations. Typically, the patient has a CFTR mutation which is R117H or G551D.

Other mutations of CFTR are classified as class I, class II, class V and class VI CFTR mutations. For class I mutations, no CFTR is produced. Examples of class I mutations include G542X, W1282X, R553X and 621+1G→T. For patients having a class II CFTR mutation, there is a defect in trafficking of the CFTR protein to the plasma membrane. Examples of class II mutations include F508del (ΔF508), N1303K, I507del (ΔI507) and R560T. For class V mutations, the synthesis of CFTR is reduced. Examples of class V mutations include 3849+10kbC→T, 2789+5G→A, 3120+1G→A and 5T. For patients having a class VI CFTR mutation, there is a decrease in the stability of the CFTR protein produced. Examples of class VI mutations include 4326delTC, Q1412X and 4279insA.

The patient may have a homozygous or heterozygous CFTR mutation. Often, the patient is homozygous or heterozygous with a class III or class IV mutation. Typically the patient is homozygous with two copies of a class III or class IV mutation or heterozygous with a copy of a class III or class IV mutation and a copy of a class I, II, V or VI mutation.

The patient may be class III/class I heterozygous, class IV/class I heterozygous, class III/class II heterozygous, class IV/class II heterozygous, class III/class V heterozygous, class IV/class V heterozygous, class III/class VI heterozygous or class IV/class VI heterozygous, where class X/class Y heterozygous means that one allele carries a class X CFTR mutation and the other allele carries a class Y mutation. For example, the patient may be heterozygous with one allele displaying the R117H CFTR mutation and the other allele displaying the ΔF508 CFTR mutation. Alternatively, the patient may be heterozygous with one allele displaying the G551D CFTR mutation and the other allele displaying the ΔF508 CFTR mutation.

As mentioned above, a side effect observed with the use of some drugs active in modulating CFTR is diarrhoea. Diarrhoea is an unpleasant side effect which can limit the use of a drug in treating a disease or condition as a patient may be unwilling or unable to take the drug in view of this side effect. This is particularly the case for patients who are already suffering from or susceptible to diarrhoea.

Clinical studies show that RPL554 does not cause diarrhoea in patients. Accordingly, RPL554 may be used to treat a patient who is susceptible to, or suffering from, diarrhoea. Susceptibility to diarrhoea may be due to one of a number of causes, for instance an inherited susceptibility to diarrhoea, susceptibility to diarrhoea due to environmental factors, or a susceptibility to diarrhoea caused by a pre-existing condition. A pre-existing condition of this type is typically a condition of the digestive system.

Typically, said patient suffering from or susceptible to diarrhoea is a patient suffering from ulcerative colitis, Crohn's disease, microscopic colitis, celiac disease, irritable bowel syndrome, bile acid malabsorption, or diverticulitis. Diarrhoea may be caused by a number of conditions such as viral infections, bacterial infections, ulcerative colitis, Crohn's disease, microscopic colitis, celiac disease, irritable bowel syndrome, bile acid malabsorption, diverticulitis or allergies.

Pharmaceutical Composition

RPL554 may be present in a pharmaceutical composition. Typically, the pharmaceutical composition may comprise RPL554 and one or more pharmaceutically acceptable carriers, diluents or excipients. The pharmaceutical composition may be as described below.

Pharmaceutical compositions may be administered to the subject by any acceptable route of administration including, but not limited to, inhaled, oral, nasal, topical (including transdermal) and parenteral modes of administration. Administration by inhalation is preferred. Further, the compositions of the invention may be administered in multiple doses per day, in a single daily dose or a single weekly dose. It will be understood that any form of the active agents used in the composition of the invention, (i.e. free base, pharmaceutically acceptable salt, solvate, etc.) that is suitable for the particular mode of administration can be used in the pharmaceutical compositions discussed herein.

The pharmaceutical compositions of this invention typically contain a therapeutically effective amount of an active agent. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount. In one embodiment, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In another embodiment, a composition suitable for inhalation, for example, comprises from about 0.01-30 wt % or active agent with yet another embodiment comprises from about 0.01-10 wt % active agent.

Any conventional carrier or excipient may be used in the pharmaceutical compositions of the invention. The choice of a particular carrier or excipient, or combinations of carriers or excipients, will depend on the mode of administration being used to treat a particular subject or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions. Pharmaceutical compositions are typically prepared by thoroughly and intimately mixing or blending the active agent/active ingredient with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

Typically, the pharmaceutical compositions are suitable for inhaled administration. The pharmaceutical composition may be for administration by nebulizer, dry powder inhaler (DPI) or metered-dose inhaler (MDI).

Suitable compositions for inhaled administration will typically be in the form of an aerosol or a powder, for instance a dry powder composition. Such compositions are generally administered using well-known delivery devices, such as a nebulizer inhaler, a dry powder inhaler, or a metered-dose inhaler, examples of which are described below.

Alternatively, a composition comprising the active agent(s)/active ingredient(s) may be administered by inhalation using a nebulizer inhaler. Such nebulizer devices typically produce a stream of high velocity air that causes the composition to spray as a mist that is carried into a subject's respiratory tract. Accordingly, when formulated for use in a nebulizer inhaler, the active agent(s)/active ingredient(s) is typically dissolved in a suitable carrier to form a solution. Alternatively, the active agent(s)/active ingredient(s) can be micronized and combined with a suitable carrier to form a suspension of micronized particles of respirable size, where micronized is typically defined as having particles in which at least about 90 percent of the particles have a mass median diameter of less than about 10 μm. The term "mass median diameter" means the diameter such that half the mass of the particles is contained in particles with larger diameter and half is contained in particles with smaller diameter.

Suitable nebulizer devices include the Respimat® Soft Mist™ Inhaler (Boehringer Ingelheim), the AERx® Pulmonary Delivery System (Aradigm Corp.), and the PARI LC Plus Reusable Nebulizer (Pari GmbH). An exemplary composition for use in a nebulizer inhaler comprises an isotonic aqueous solution comprising from about 0.05 μg/mL to about 10 mg/mL of RPL554 or a pharmaceutically acceptable acid addition salt thereof. In one embodiment, such a solution has a pH of about 3.5 to 6.0.

Alternatively, a composition comprising the active agent(s)/active ingredient(s) may be administered by inhalation using a dry powder inhaler (DPI). Such DPIs typically administer the active agent as a free-flowing powder that is dispersed in a subject's air-stream during inspiration. In order to achieve a free flowing powder, the active agent(s)/active ingredient(s) is typically formulated with a suitable excipient such as lactose, starch, mannitol, dextrose, polylactic acid, polylactide-co-glycolide, and combinations thereof. Typically, the active agent(s)/active ingredient(s) is micronized and combined with an excipient to form a blend suitable for inhalation. Accordingly, in one embodiment of the invention, the active agent(s)/active ingredient(s) is in micronized form. For example, a representative composition for use in a DPI comprises dry lactose having a particle size between about 1 μm and about 100 μm (e.g., dry milled lactose) and micronized particles of the active agent. Such a dry powder formulation can be made, for example, by combining lactose with the active agent and then dry blending the components. Alternatively, if desired, the active agent can be formulated without an excipient. The composition is then typically loaded into a DPI, or into inhalation cartridges or capsules for use with a DPI. DPIs are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Diskus® or Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Alternatively, the composition comprising the active agent may be administered by inhalation using a metered-dose inhaler (MDI). Such MDIs typically discharge a measured amount of the active agent using compressed propellant gas. Metered-dose formulations thus typically comprise a solution or suspension of the active agent in a liquefied propellant, such as a chlorofluorocarbon such as CCl3F or a hydrofluoroalkane (HFA) such as 1,1,1,2-tetrafluoroethane (HFA 134a) and 1,1,1,2,3,3,3-heptafluoro-n-propane (HFA 227), although HFAs are generally preferred due to concerns about chlorofluorocarbons affecting the ozone layer. Additional optional components of HFA formulations include co-solvents, such as ethanol or pentane, and surfactants, such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company). A representative composition for use in an MDI comprises from about 0.01-5 wt % of active agent; from about 0-20 wt % ethanol; and from about 0-5 wt % surfactant; with the remainder being an HFA propellant. Such compositions are typically prepared by adding a chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of the MDI. MDIs are well known to those of ordinary skill in the art, and many such devices are commercially available, with representative devices including AeroBid Inhaler System (Forest Pharmaceuticals), Atrovent Inhalation Aerosol (Boehringer Ingelheim), Flovent® (GlaxoSmithKline), Maxair Inhaler (3M), Proventil® Inhaler (Schering), Serevent® Inhalation Aerosol (GlaxoSmithKline), and the like. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.).

Additional examples of processes of preparing respirable particles, and formulations and devices suitable for inhalation dosing are described in U.S. Pat. No. 5,874,063 to Briggner et al.; U.S. Pat. No. 5,983,956 to Trofast; U.S. Pat. No. 6,221,398 to Jakupovic et al.; U.S. Pat. No. 6,268,533 to Gao et al.; U.S. Pat. No. 6,475,524 to Bisrat et al.; and U.S. Pat. No. 6,613,307 to Cooper.

Alternatively, the pharmaceutical compositions may be suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (i.e., as capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions that can be used include polymeric substances and waxes. The active agent can also be in microencapsulated form, if appropriate, with one or more of the above-described excipients. Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a subject, i.e., each unit containing a predetermined quantity of the active agents calculated to produce the desired therapeutic effect either alone or in combination with one or more additional units. For example, such unit dosage forms may be capsules, tablets, pills, and the like.

Compositions of the invention can also be administered parenterally (e.g., by subcutaneous, intravenous, intramuscular, or intraperitoneal injection). For such administration, the active agents are provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. A typical parenteral formulation is a sterile pH 4-7 aqueous solution of the active agents. Parenteral formulations may also contain one or more solubilizers, stabilizers, preservatives, wetting agents, emulsifiers, and dispersing agents. These formulations may be rendered sterile by use of a sterile injectable medium, a sterilizing agent, filtration, irradiation, or heat.

Compositions of the invention can also be administered transdermally using known transdermal delivery systems and excipients. For example, the active agents can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Dosage

A therapeutically effective amount of a compound as described herein is administered to a patient. In the treatments according to the invention, RPL554 or the pharmaceutically acceptable acid addition salt thereof may be provided in any suitable dosage. A typical dose is from 0.1 µg to 100 mg according to the activity of the specific compound, the age, weight and conditions of the subject to be treated, the type and severity of the disease and the frequency and route of administration. The amount of RPL554 present in a single dose may be from 1 µg to 50 mg, from 1 µg to 10 mg, from 1 µg to 1 mg, from 1 µg to 500 g, from 1 µg to 100 µg or from 1 µg to 50 µg (i.e. 0.001 mg to 0.050 mg). Alternatively, the amount of RPL554 present in a single dose may be from 1 µg to 50 mg, from 10 µg to 50 mg, from 100 µg to 50 mg or from 250 µg to 50 mg. The dose of RPL554 may be from 1 µg/kg to 500 µg/kg, or from 50 µg/kg to 250 µg/kg (kg as weight of patient). A dose may be administered as often as required. This may be as and when a dose is required, or may follow a routine such as three or more times daily, twice daily, once daily, three or more times weekly, twice weekly, or once weekly.

Preferably, the active agent for modulating CFTR is administered by inhalation.

Treatment with an active compound as described herein typically comprises administering a therapeutically effective amount of the active compound(s).

Combination

It is a finding of the invention that RPL554 and leukotriene receptor antagonists have an additive or synergistic effect in activating CFTR. Combinations of drugs in which active ingredients operate via different physiological pathways and yet achieve an additive or synergistic activity are particularly useful. Frequently, the therapeutic advantage arises because the combination can achieve a therapeutically useful effect using lower concentrations of each active component. This enables the side-effects of the medication to be minimised. Thus, the combination can be formulated so that each active ingredient is present at a concentration which is subclinical in cells other than the target disease cells. The combination is nevertheless therapeutically effective in target cells that respond to both ingredients.

The invention therefore provides a composition comprising RPL554 and a leukotriene receptor antagonist. The leukotriene receptor antagonist is typically a leukotriene D4 receptor antagonist. Preferably, the leukotriene receptor antagonist is a multidrug resistance-associated protein 4 (MRP4) inhibitor.

The leukotriene receptor antagonist may be MK-571, MK-886, montelukast, zafirlukast or pranlukast.

The composition comprising the two active ingredients as defined herein may be a pharmaceutical composition. The composition may further comprise one or more pharmaceutically acceptable carriers, diluents or excipients. The one or more pharmaceutically acceptable carriers, diluents or excipients may be as defined herein. The composition may be administered as described herein. For instance, the composition may be administered by inhalation.

The two active ingredients may be in fixed or free combination. Preferably, the two active ingredients are in fixed combination. For instance, they may be intermixed.

The invention provides a composition as defined herein for use in treating or preventing a disease or condition as defined herein in a patient as defined herein by modulating CFTR activity.

The invention provides use of 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof in the manufacture of a medicament for use in treating or preventing a disease or condition as defined herein in a patient as defined herein by modulating CFTR activity in combination with a leukotriene receptor antagonist as defined herein.

The invention provides use of a leukotriene receptor antagonist as defined herein in the manufacture of a medicament for use in treating or preventing a disease or condition as defined herein in a patient as defined herein by modulating CFTR activity in combination with 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof.

The dose of each of the active ingredients may independently as described above for RPL554. The combination of the two active ingredients, or each ingredient alone, may be administered by inhalation as defined herein.

It is also a finding of the invention that (i) RPL554 and (ii) a CFTR potentiator or CFTR corrector have an additive or synergistic effect in activating or potentiating CFTR. The invention thus provides a composition comprising RPL554 or a pharmaceutically acceptable acid addition salt thereof and a CFTR potentiator. The invention also provides a composition comprising RPL554 or a pharmaceutically acceptable acid addition salt thereof and a CFTR corrector.

The composition comprising the two active ingredients as defined herein may be a pharmaceutical composition. The composition may further comprise one or more pharmaceutically acceptable carriers, diluents or excipients. The one or more pharmaceutically acceptable carriers, diluents or excipients may be as defined herein. The composition may be administered as described herein. For instance, the composition may be administered by inhalation.

The two active ingredients may be in fixed or free combination. Preferably, the two active ingredients are in fixed combination. For instance, they may be intermixed.

The CFTR potentiator may be any suitable CFTR potentiator. For instance, the CFTR potentiator may be VX770 (Ivacaftor), QBW251, NPPB (5-nitro-2-(3-phenylpropylamino)-benzoate), VRT532 (4-methyl-2-(5-phenyl-1H-pyrazol-3-yl)phenol), PG-01 (N-methyl-N-[2-[[4-(1-Methylethyl)phenyl]amino]-2-1H-indole-3-acetamide), or a pharmaceutically acceptable acid addition salt of one of these compounds. VX-770 or a pharmaceutically acceptable acid addition salt thereof is preferred. The known drug VX-770 (Ivacaftor, Kalydeco®) is approved for the treatment of cystic fibrosis in patients with the G551D mutation and has the structure

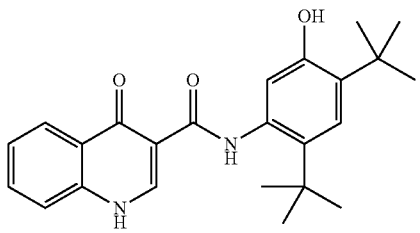 [SMILES: CC(C)(C)c1cc(C(C)(C)C)c(NC(=O)c2c[nH]c3ccccc3c2=O)cc1O]

and formula N-(2,4-di-tert-butyl-5-hydroxyphenyl)-4-oxo-1,4-dihydroquinoline-3-carboxamide.

The CFTR corrector may be any suitable CFTR corrector or any pharmaceutically acceptable acid addition salt thereof. For instance, the CFTR corrector is typically VX809 (Lumacaftor, 3-{6-{[1-(2,2-Difluoro-1,3-benzodioxol-5-yl)cyclopropanecarbonyl]amino}-3-methylpyridin-2-yl}benzoic acid), VX661 (1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), Corr-4a (N-{2-[(5-chloro-2-methoxyphenyl)amino]-4'-methyl-4,5'-bi-1,3-thiazol-2'-yl}benzamide), VRT532 (4-methyl-2-(5-phenyl-1H-pyrazol-3-yl)phenol) or a pharmaceutically acceptable acid addition salt of one of these compounds. Lumacaftor or a pharmaceutically acceptable acid addition salt thereof is preferred.

The invention therefore provides a composition comprising (i) RPL554 or a pharmaceutically acceptable acid addition salt thereof and (ii) a CFTR potentiator or a CFTR corrector. Typically, component (ii) is a CFTR potentiator.

The invention also provides a product comprising (a) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof and (b) a CFTR potentiator or a CFTR corrector for simultaneous, separate or sequential use in treating or preventing a disease or condition as defined herein in a patient as defined herein by modulating CFTR activity.

Typically, the product comprises (a) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof and (b) N-(2,4-di-tert-butyl-5-hydroxyphenyl)-4-oxo-1,4-dihydroquinoline-3-carboxamide or a pharmaceutically acceptable acid addition salt thereof for simultaneous, separate or sequential use in treating or preventing a disease or condition as defined herein in a patient as defined herein by modulating CFTR activity.

The invention also provides 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof for use in treating or preventing a disease or condition as defined herein in a patient as defined herein by modulating CFTR activity in combination with a CFTR potentiator or a CFTR corrector.

The invention also provides a CFTR potentiator or a CFTR corrector for use in treating or preventing a disease or condition as defined herein in a patient as defined herein by modulating CFTR activity in combination with 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof.

The invention also provides use of 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof in the manufacture of a medicament for use in treating or preventing a disease or condition as defined herein in a patient as defined herein by modulating CFTR activity in combination with a CFTR potentiator or a CFTR corrector.

The invention also provides use of a CFTR potentiator or a CFTR corrector in the manufacture of a medicament for use in treating or preventing a disease or condition as defined herein in a patient as defined herein by modulating CFTR activity in combination with 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof.

The invention also provides a method of treating or preventing a disease or condition as defined herein in a patient as defined herein by modulating CFTR activity, which method comprises administering to the patient (a) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof and (b) a CFTR potentiator or a CFTR corrector.

The patient to be treated by the combination of RPL554 and a CFTR potentiator or corrector typically has a CFTR mutation which may be a class III or a class IV CFTR mutation. As discussed above, RPL554 is particularly effective in modulating the activity of CFTR resulting from gating or conductance mutations such as class III and class IV CFTR mutations respectively. CFTR potentiators and CFTR correctors can be effective in correcting or potentiating the activity of CFTR resulting from mutations other than gating and conductance mutations, for instance class I, II, V or VI mutations as defined above. CFTR correctors can be particularly effective in correcting the activity of CFTR resulting from class II CFTR mutations.

Patients suffering from cystic fibrosis and other disorders related to CFTR may be homozygous or heterozygous carriers of defective CFTR genes. Often, patients suffering from cystic fibrosis are homozygous carriers of the ΔF508 mutation. The combination of RPL554 and a CFTR potentiator or corrector can be particularly effective in treating patients who are heterozygous carriers of CFTR mutations. In particular, heterozygous patients having a gating or conductance mutation on one allele and a different (non-gating or non conductance) CFTR mutation on the other allele can be treated using this combination because the CFTR corrector corrects the trafficking defects and RPL554 modulates the activity of defects arising from gating or conductance mutations. For instance, the patient may be heterozygous with one allele displaying a class III or class IV CFTR mutation and the other allele displaying a class II CFTR mutation. The patient may be class III/class I heterozygous, class IV/class I heterozygous, class III/class II heterozygous, class IV/class II heterozygous, class III/class V heterozygous, class IV/class V heterozygous, class III/class VI heterozygous or class IV/class VI heterozygous, where class X/class Y heterozygous means that one allele carries a class X CFTR mutation and the other allele carries a class Y mutation. For example, the patient may be heterozygous with one allele displaying the R117H CFTR mutation and the other allele displaying the ΔF508 CFTR mutation. Alternatively, the patient may be heterozygous with one allele displaying the G551D CFTR mutation and the other allele displaying the ΔF508 CFTR mutation.

The dose of each of the active ingredients may independently be as described above for RPL554. The combination of the two active ingredients, or each ingredient alone, may be administered by inhalation as defined herein.

The following Examples illustrate the invention. They do not however, limit the invention in any way. In this regard, it is important to understand that the particular assays used in the Examples section are designed only to provide an indication of activity. There are many assays available to determine such activity, and a negative result in any one particular assay is therefore not determinative.

EXAMPLES

Example 1—Test of Activator Activity on WT CFTR in CFBE Monolayers

Figure 2:
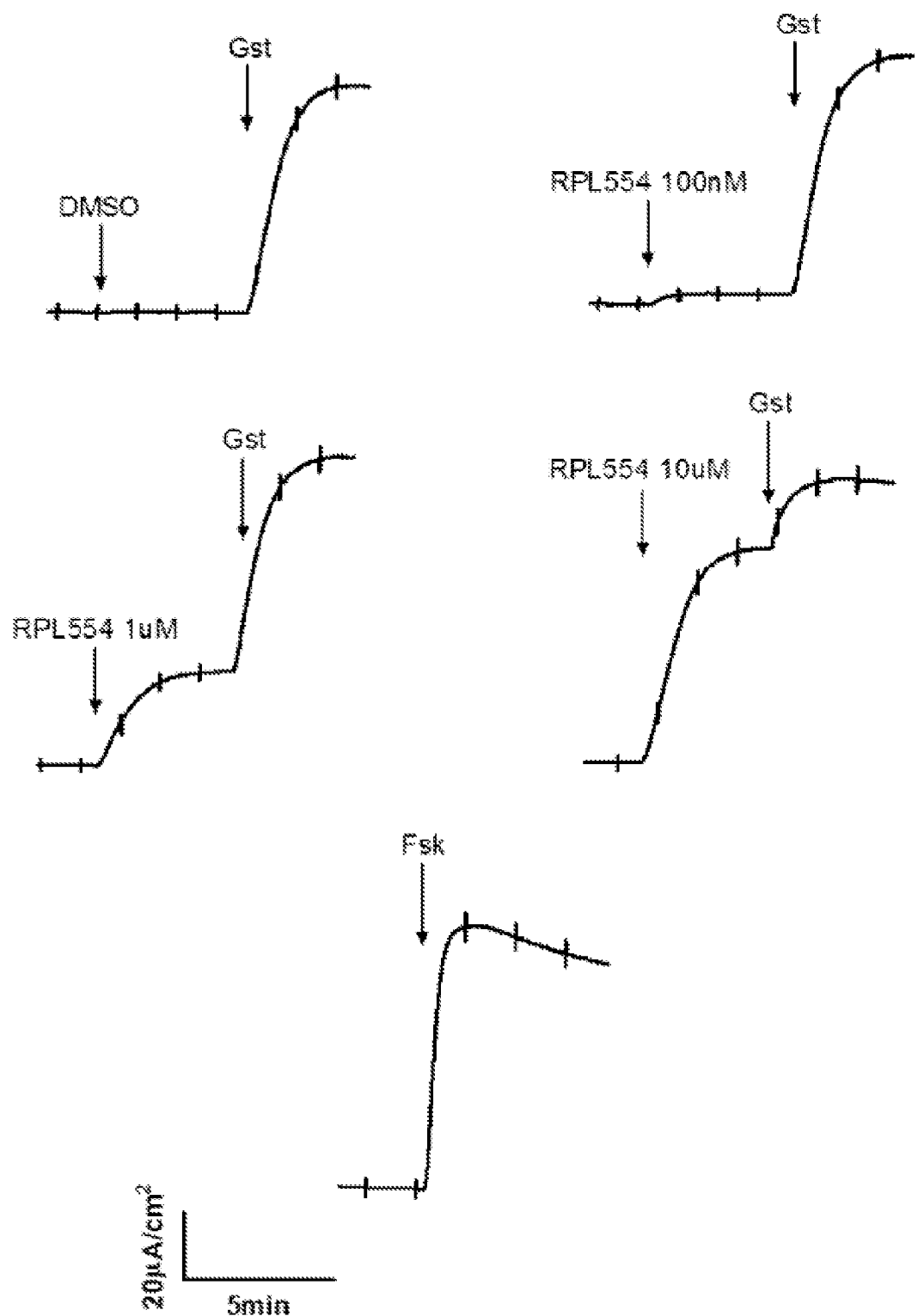
FIG. 2 shows timecourses for activation of WT CFTR in CFBE cell monolayers by RPL554, genistein, and forskolin.

RPL554 was added acutely at three different concentrations (0.1, 1.0, 10 μM) to cystic fibrosis bronchial epithelial (CFBE) monolayers expressing WT CFTR. DMSO dimethylsulfoxide) was used as a negative control. Genistein (50 μM) and forskolin (10 μM) were used as positive controls. The results are shown in FIGS. 1 and 2 which demonstrate that RPL554 alone can activate WT CFTR channels in CFBE monolayers.

Example 2—Test of Activator Activity on WT CFTR in Primary HBE Cells

Figure 3:
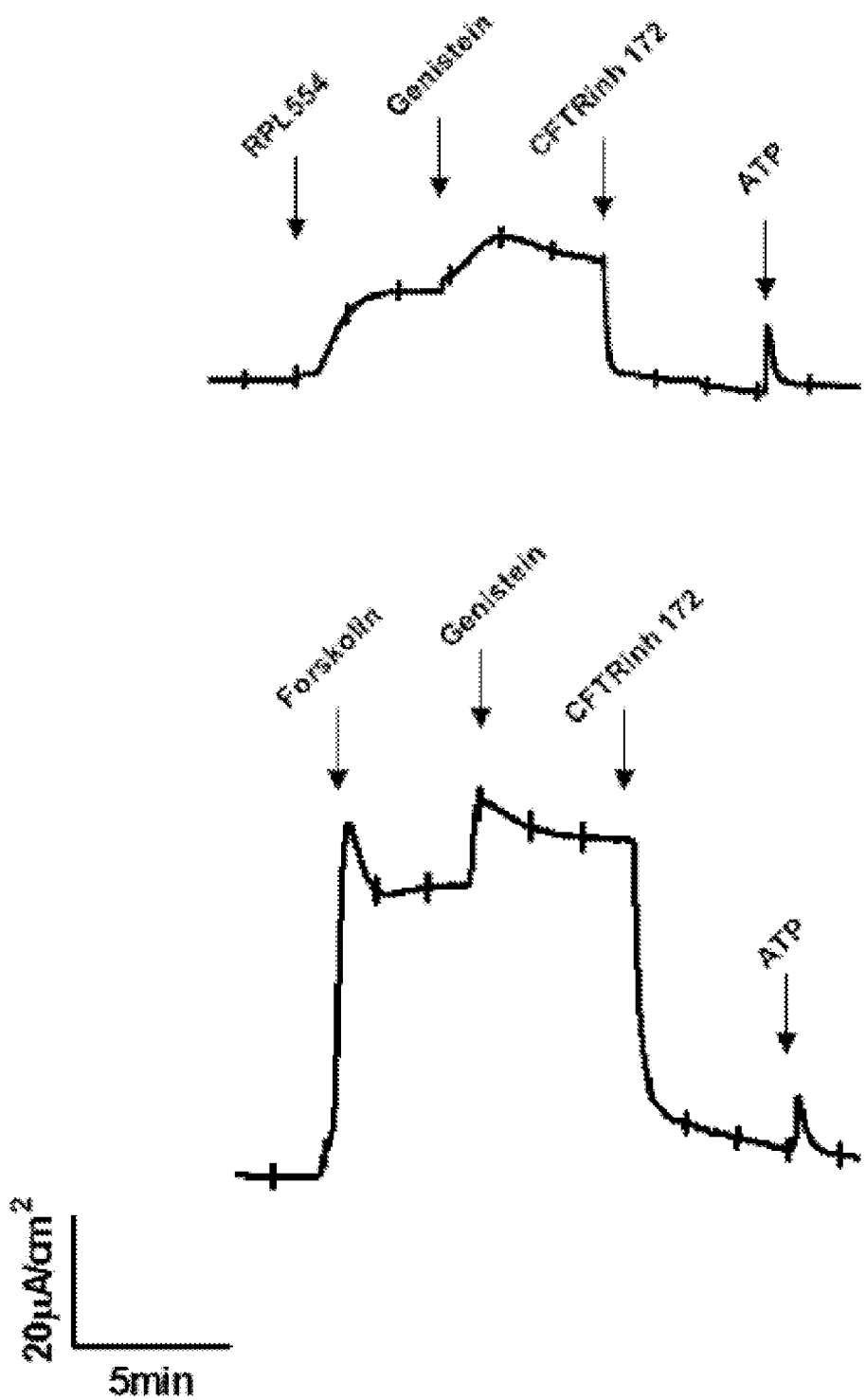
FIG. 3 shows timecourses for activation of WT CFTR in primary human bronchial epithelial (HBE) cells.

After pretreatment with 100 nM amiloride to inhibit ENaC currents, RPL554 or forskolin (10 μM; apical) was added, followed sequentially by genistein (50 μM; apical), CFTRinh-172 and ATP (100 μM). The results are shown in FIG. 3 which demonstrate that RPL554 alone can activate WT CFTR channels in highly differentiated primary HBE monolayers.

Figure 4:
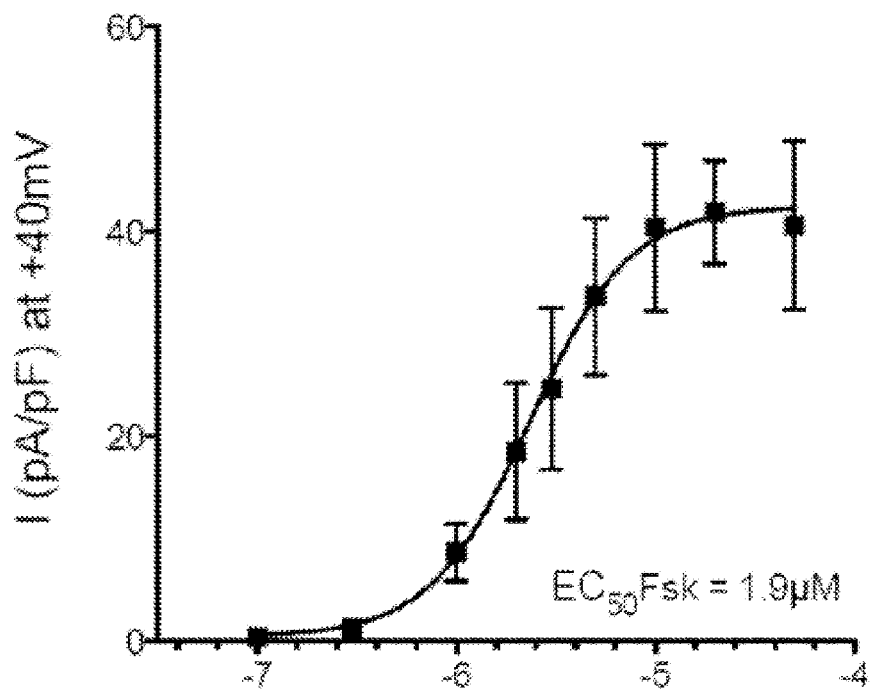
FIG. 4 shows forskolin (Fsk) concentration-response for CFTR current in Chinese hamster ovary (CHO) cells.

Example 3—RPL554 Tested as an Enhancer of WT CFTR in CHO Cells Using the Whole Cell Patch Clamp Technique A forskolin (Fsk) concentration giving a submaximal response was determined. Forskolin-stimulated currents were measured at concentrations between 100 nM and 50 μM and fitted to determine the EC50 (FIG. 4). It was then confirmed that the current was due to CFTR.

Figure 5:
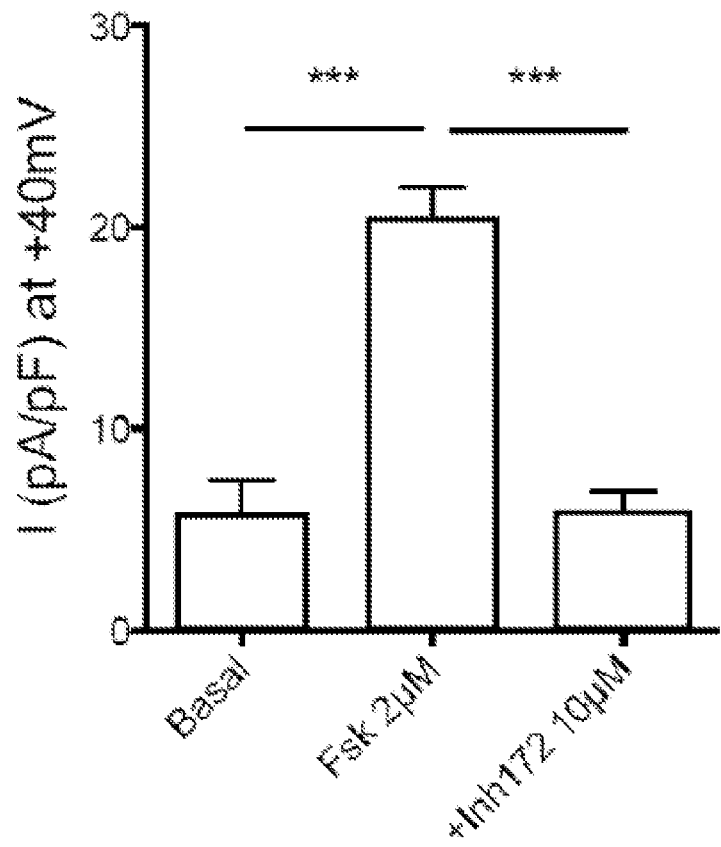
FIG. 5 shows sensitivity of CFTR in CHO cells to the CFTR inhibitor Inh-172.

To determine if the current induced by 2 μM forskolin was indeed carried by CFTR channels, the sensitivity of the current at +40 mV to the CFTR inhibitor CFTRinh-172 (Inh 172) was examined (FIG. 5).

Figure 6:
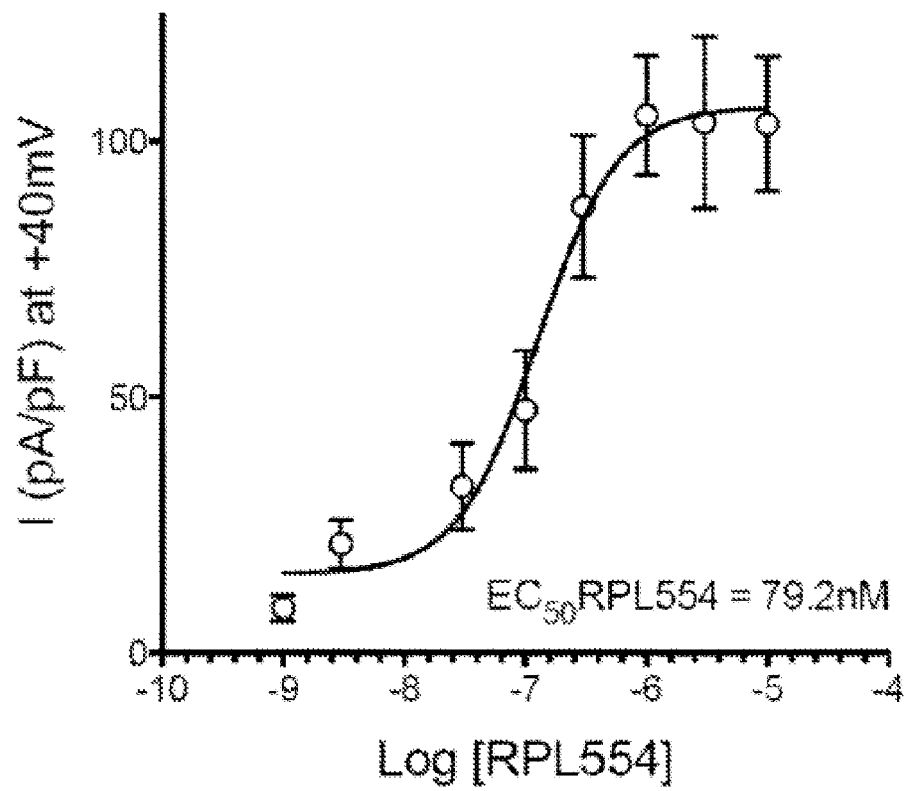
FIG. 6 shows concentration dependence of RPL554 as an enhancer of CFTR in CHO cells.

RPL554's ability to enhance the response of WT CFTR to 2 μM forskolin in whole cell patches was then assessed. To examine the effect of RPL554 on CFTR activity during submaximal stimulation, CHO cells were stimulated with 2 μM forskolin then exposed acutely to RPL554. The concentration dependence of RPL554 as an enhancer of CFTR is shown in FIG. 6.

Figure 7:
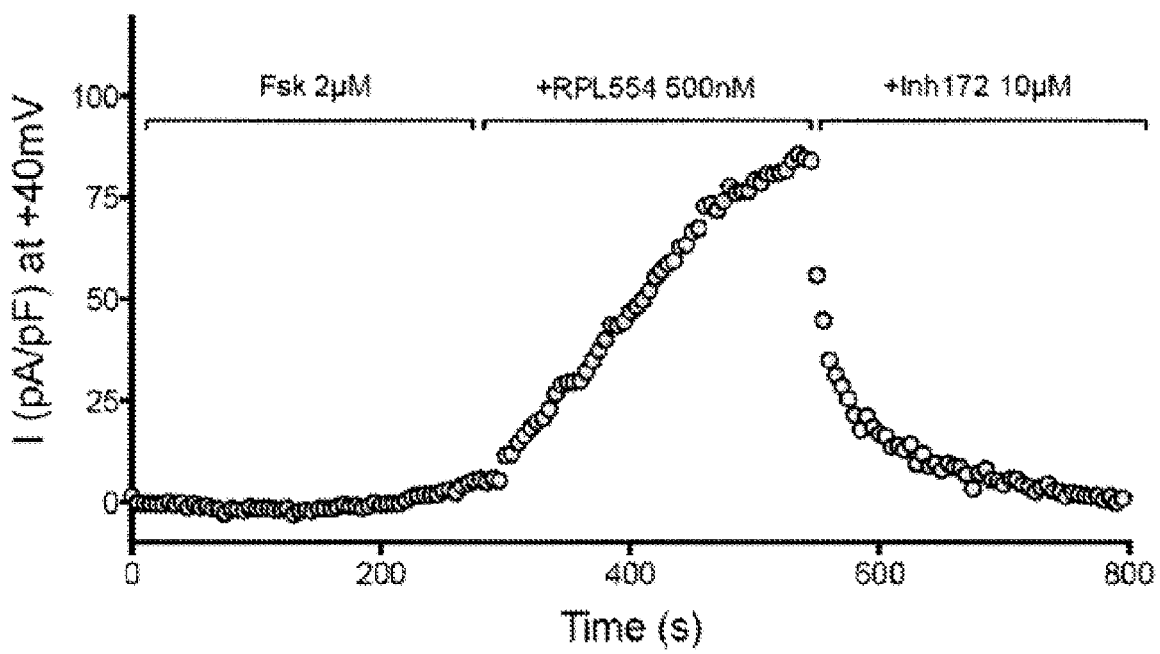
FIG. 7 shows the timecourse of CFTR activation by RPL554 and inhibition by Inh-172.

The timecourse of CFTR activation by RPL554 and inhibition by Inh 172 (current at +40 mV normalized to that with 2 μM forskolin) in FIG. 7 shows the RPL554 response under these conditions. The sensitivity to CFTRinh-172 confirms it is mediated by CFTR channels.

Example 4—Comparison of the Modulation of WT CFTR Activity in CHO Cells by RPL554 and an Approved Potentiator (VX770, Kalydeco®)

Figure 8:
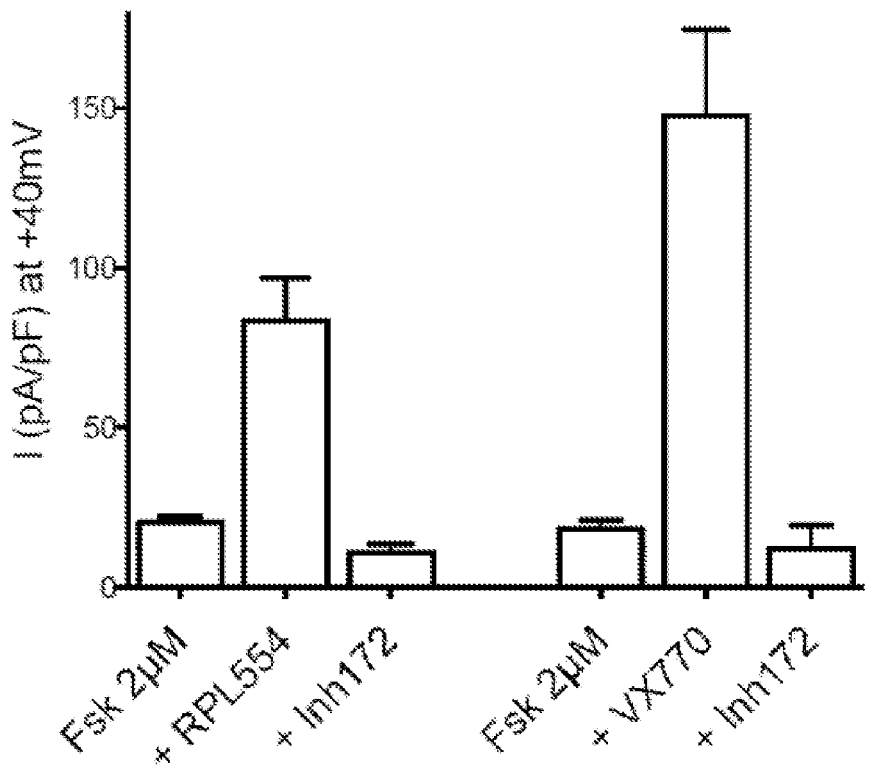
FIG. 8 shows comparison of RPL554 and VX770 effects on WT CFTR in CHO cells during sub-maximal forskolin stimulation.

The effects on WT CFTR in CHO cells during submaximal forskolin stimulation were compared for RPL554 and VX770 (FIG. 8). RPL554 enhances WT CFTR channel activity CHO cells, and this response is >50% that of VX770.

Example 5—Potentiation of CFBE ΔF508-CFTR Cells

Figure 9:
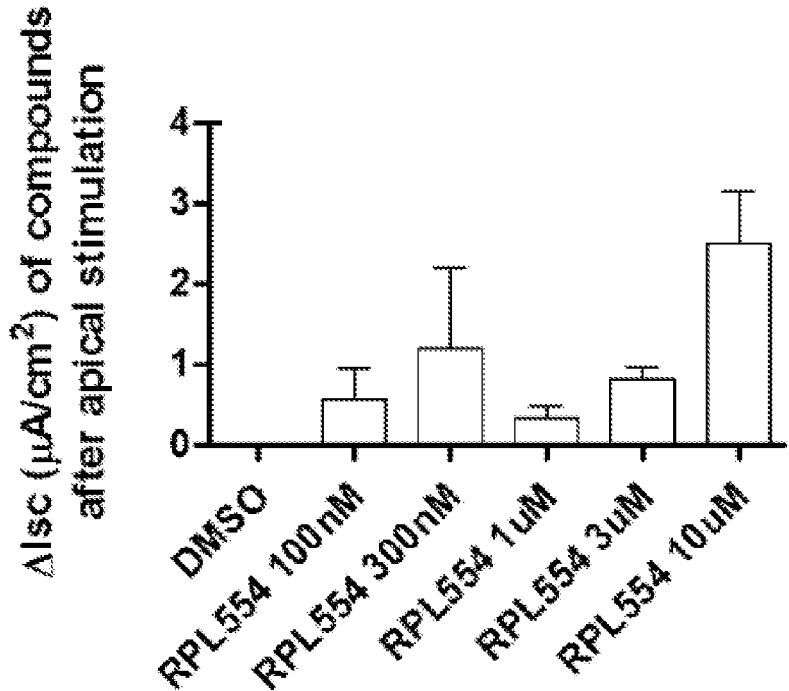
FIG. 9 shows potentiator activity results for RPL554 in CFBE cells expressing ΔF508 CFTR.

CFBE ΔF508-CFTR cells were incubated at 29° C. for 24 hours to partially rescue CFTR. Cells were stimulated with 10 μM forskolin on apical side and then with RPL554 at 100 nM, 300 nM, 1 μM, 3 μM, and 10 μM, with DMSO used as a control. The results are shown in FIG. 9 which demonstrates that RPL554 potentiates CFBE ΔF508-CFTR cells.

Example 6—Enhancement of WT-CFTR Activation in CFBE Cells by RPL554

Figure 10:
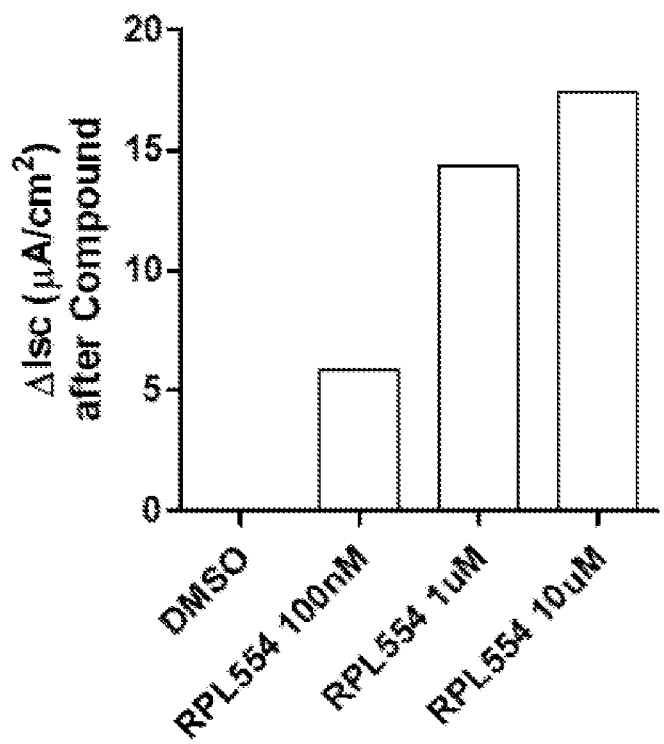
FIG. 10 shows enhancement of WT CFTR in CFBE WT cells after 1 µM forskolin.
Figure 11:
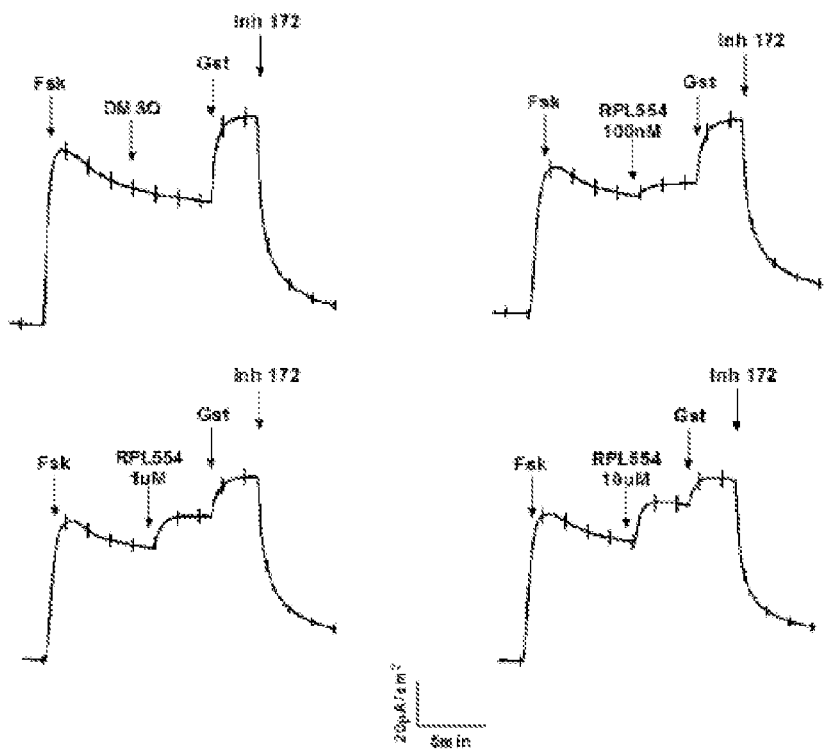
FIG. 11 shows timecourses for RPL554 enhancement of WT-CFTR in CFBE WT cells after stimulation with forskolin.

CFBE cells were cultured in ALI for one week until they were polarized. Cells were stimulated apically with forskolin, then with RLP554 and Genestein as shown in FIGS. 10 and 11. RPL554 acts as an enhancer of WT-CFTR.

Figure 12:
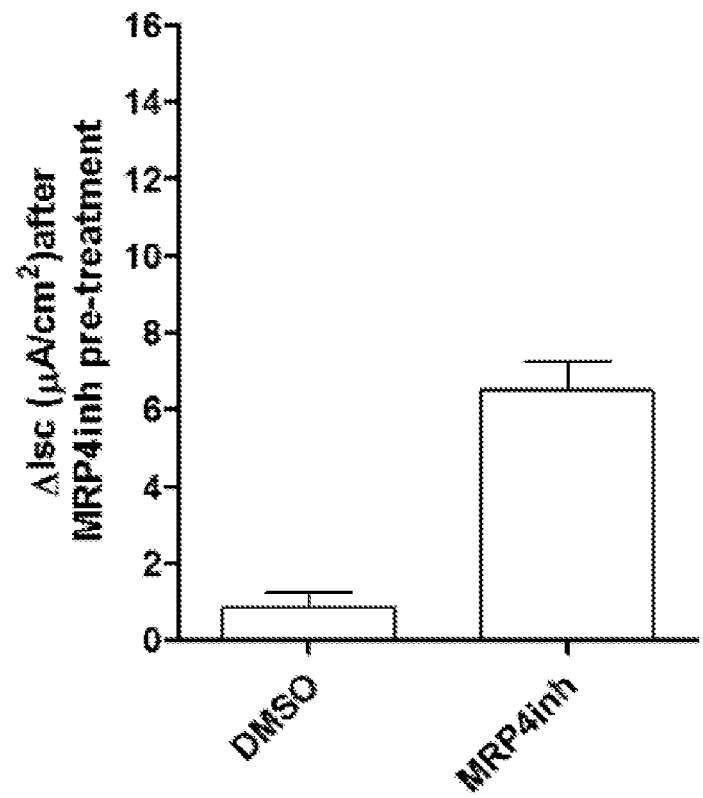
FIG. 12 shows stimulation of Cl-currents by MRP4 inhibitor (MK571) in low temperature corrected CFBE ΔF508-CFTR cells.
Figure 13:
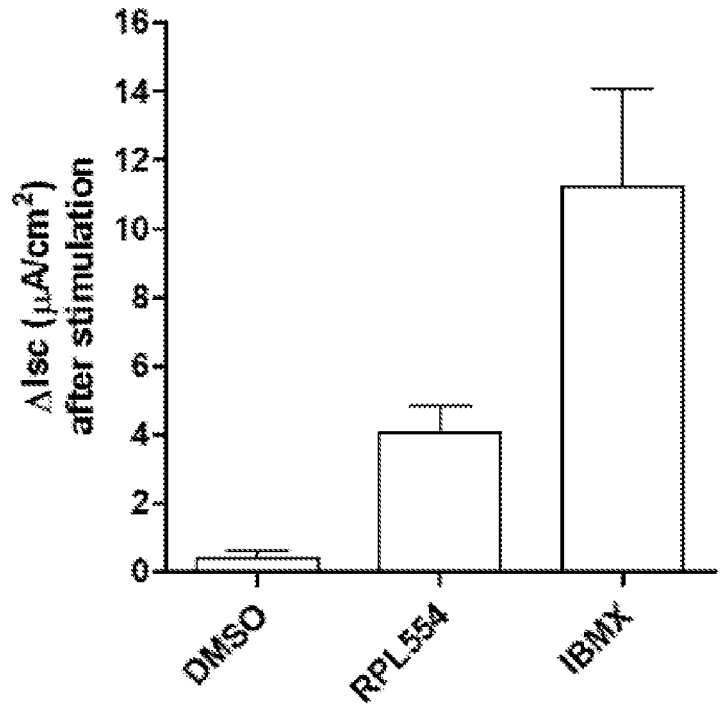
FIG. 13 shows activation by RPL554 of Cl-currents by RPL554 in low temperature corrected CFBE ΔF508-CFTR cells.
Figure 14:
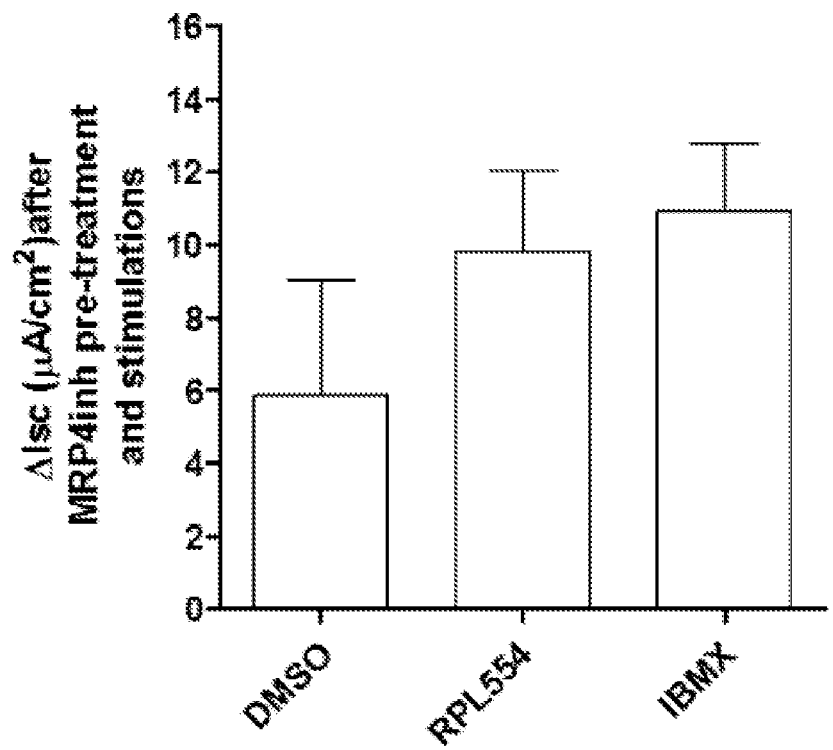
FIG. 14 shows results for MK571 (MRP4inh)+stimulation for DMSO, RPL554 and IBMX.
Figure 15:
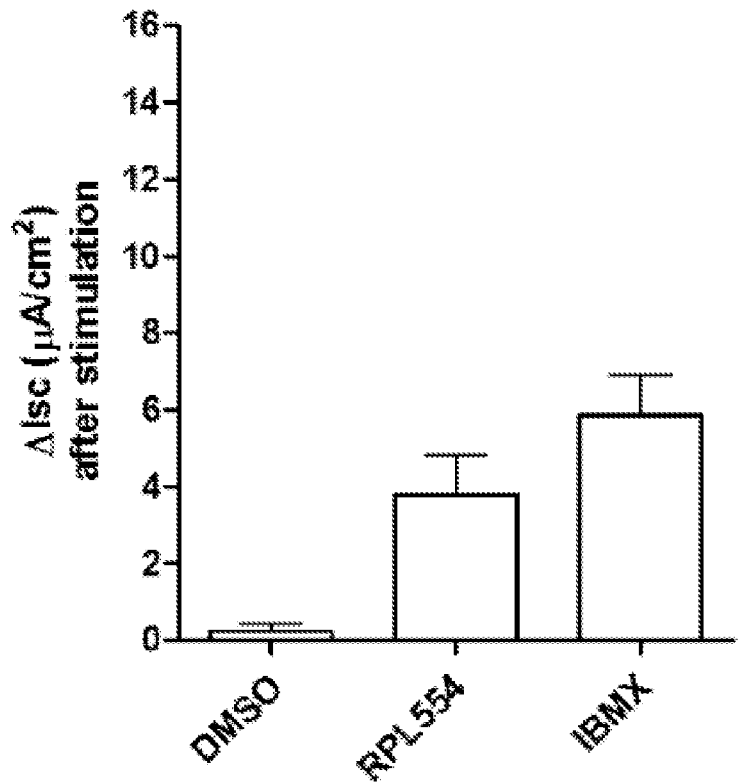
FIG. 15 shows results after MK571 (MRP4inh) pre-treatment for DMSO, RPL554 and IBMX.

Example 7—RPL554 and a Leukotriene Receptor Antagonist in CFBE ΔF508-CFTR Cells CFBE ΔF508-CFTR cells were stimulated with the leukotriene D4 receptor agonist (MRP4 inhibitor) MK571 (20 μM) and this increased CFTR-dependent Isc by 6-fold (FIG. 12) and enhanced the response to RPL554. This implies there is significant cAMP release from airway epithelial cells under basal conditions. The results for RPL554 in the absence of MRP4inh pretreatment are shown in FIG. 13. MK571 and RPL554 interact synergistically when used together (FIG. 14). MK571 and RPL554 (3 μM) caused additive increases in CFTR activity when added sequentially (FIG. 15).

These results suggest that RPL554 alone or in combination with leukotriene receptor antagonists (e.g. MRP4 blockers) may be useful as adjunct therapies in CF.

Example 8—RPL554 and VX-770 in HBE Cells from a ΔF508/R117H Patient

Figure 16:
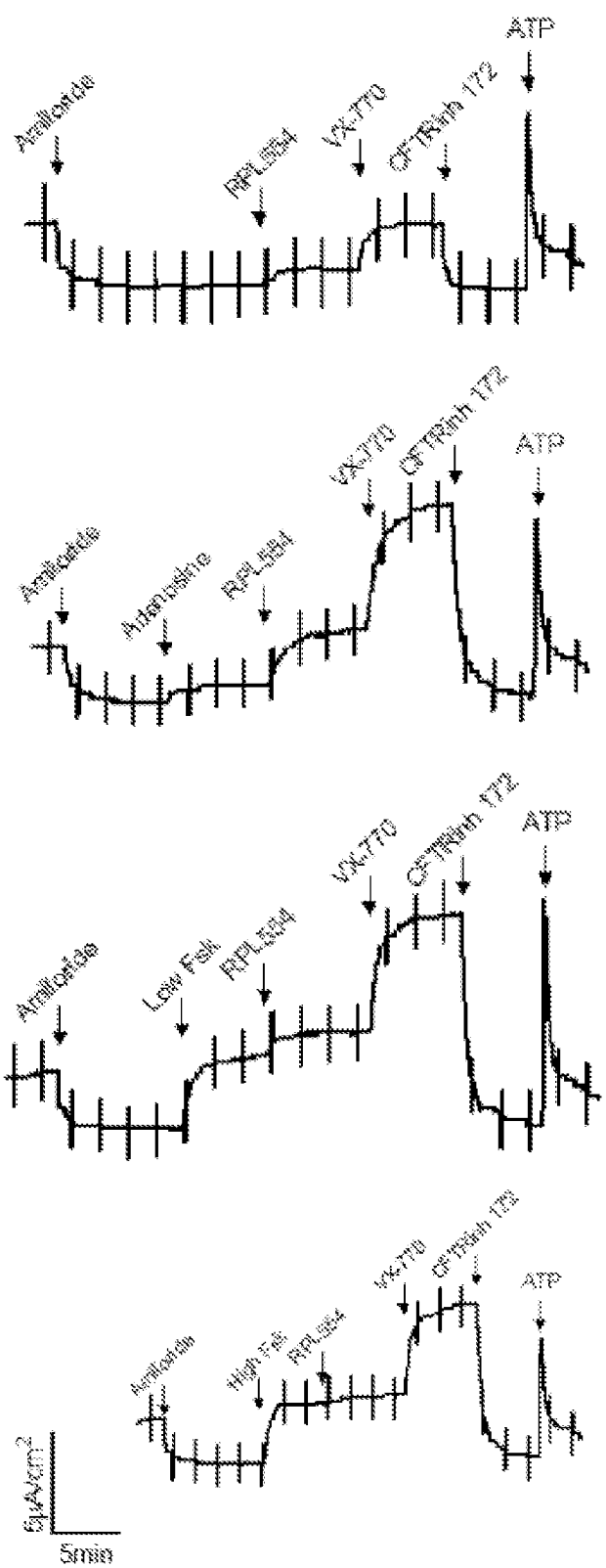
FIG. 16 shows timecourses for activation and enhancement of CFTR in HBE cells from a ΔF508/R117H patient.
Figure 17:
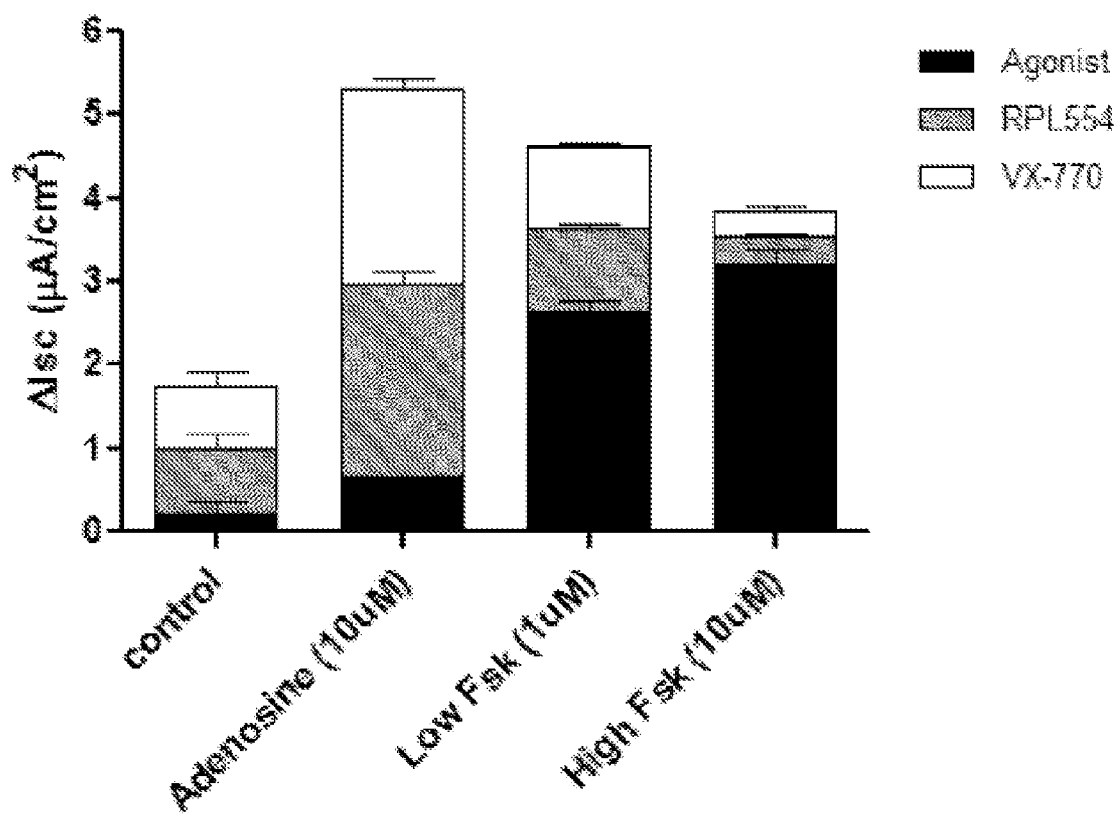
FIG. 17 shows the comparison of total activation of CFTR in HBE cells from a ΔF508/R117H patient with treatment with RPL554 and VX770 (Ivacaftor) following a control, adenosine and forskolin at low and high concentrations.

Primary HBEs from a F508del/R117H patient were grown at the air-liquid interface (ALI) until well differentiated (4 weeks), then mounted in Ussing chambers with a basolateral-to-apical Cl-gradient. Monolayers were exposed sequentially to either apical adenosine (10 μM) or forskolin (1 or 10 μM, bilaterally), then to apical RPL554 (10 μM) and finally VX-770 (100 nM) as indicated. The results over time for each treatment are shown in FIG. 16. The concentrations of the agents used were as follows: amiloride 100 μM, adenosine 10 μM, forskolin 1 μM or 10 μM, RPL554 10 μM, VX-770 100 nM, CFTRinh172 10 μM, and ATP 100 μM. The comparison of total activation is shown in FIG. 17.

It has been shown that RPL554 causes a significant enhancement of CFTR activation in these CF mutations under control conditions (with no agonist) and during physiological adenosine stimulation. The relative effect of RPL554 becomes progressively less with increasing forskolin concentrations, confirming the PDE inhibition effect of RPL554.

Example 9—Effect of RPL554 Alone and in Combination with Lumacaftor

Primary human bronchial epithelial (HBE) cells were obtained from two heterozygous R117H/ΔF508 patients (patients 1 and 2). The effect of RPL554 on the HBE cells from each of these patients was assessed using an Ussing chamber by measuring short circuit current (ISC) of CFTR-dependent Cl-transport. RPL554 was used with forskolin pre-stimulation, alone or in combination with the CFTR corrector Lumacaftor. All experiments used 2 μM forskolin, 10 μM RPL554 and 10 μM Lumacaftor.

Figure 18:
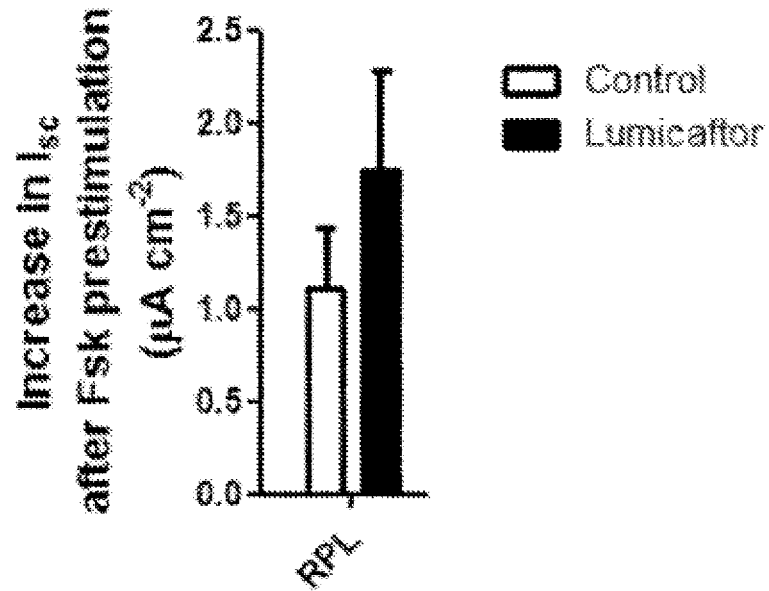
FIG. 18 shows the effect on measured ISC of RPL554 alone ("control") or in combination with Lumacaftor ("Lumacaftor") following forskolin stimulation.

The resistance of the HBE cells obtained from patient 1 was approximately 550 Ωcm-2. The effect on measured ISC of RPL554 alone ("control") or in combination with Lumacaftor ("Lumacaftor") following forskolin stimulation for HBE cells from patient 1 is shown in FIG. 18. The results shown are the mean response with n=4.

Figure 19:
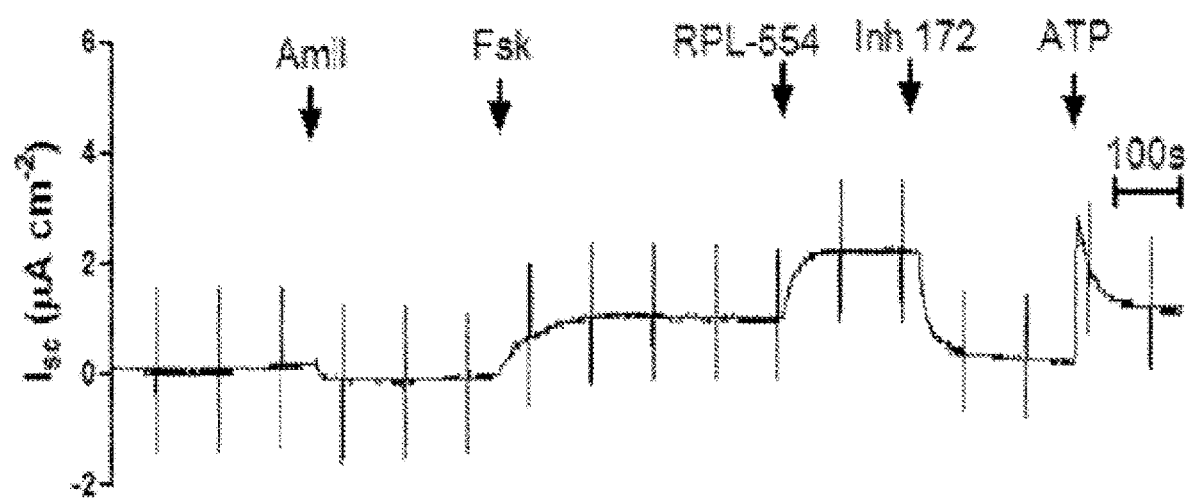
FIG. 19 shows a timecourse for RPL554 enhancement of CFTR in HBE cells after stimulation with forskolin.

The resistance of the HBE cells obtained from patient 2 was approximately 850 Ωcm-2. FIG. 19 shows a timecourse for RPL554 enhancement of CFTR in HBE cells from patient 2 after stimulation with forskolin.

What is claimed is:

1. A composition comprising (a) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof, and (b) a CFTR potentiator or a CFTR corrector.

2. A composition according to claim 1, wherein:
the CFTR potentiator is Ivacaftor (VX770, N-(2,4-di-tert-butyl-5-hydroxyphenyl)-4-oxo-1,4-dihydroquinoline-3-carboxamide), QBW251, NPPB (5-nitro-2-(3-phenylpropylamino)-benzoate), VRT532 (4-methyl-2-(5-phenyl-1H-pyrazol-3-yl)phenol), PG-01 (N-methyl-N-[2-[[4-(1-Methylethyl)phenyl]amino]-2-1H-indole-3-acetamide), or a pharmaceutically acceptable acid addition salt thereof; or
the CFTR corrector is VX809 (Lumacaftor, 3-{6-{[1-(2,2-Difluoro-1,3-benzodioxol-5-yl)cyclopropanecarbonyl]amino}-3-methylpyridin-2-yl}benzoic acid), VX661 (1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), Corr-4a (N-{2-[(5-chloro-2-methoxyphenyl)amino]-4'-methyl-4,5'-bi-1,3-thiazol-2'-yl}benzamide), VRT532 (4-methyl-2-(5-phenyl-1H-pyrazol-3-yl)phenol), or a pharmaceutically acceptable acid addition salt thereof.

3. A composition according to claim 1, wherein the CFTR potentiator or CFTR corrector is N-(2,4-di-tert-butyl-5-hydroxyphenyl)-4-oxo-1,4-dihydroquinoline-3-carboxamide (Ivacaftor) or a pharmaceutically acceptable acid addition salt thereof.

4. A method for treating or preventing cystic fibrosis in a patient, the method comprising administering a composition to the patient, which composition comprises (i) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof, and (ii) a CFTR potentiator or a CFTR corrector.

5. A method according to claim 4, wherein the patient has a CFTR mutation.

6. A method according to claim 5, wherein the CFTR mutation is a class III CFTR mutation or class IV CFTR mutation.

7. A method according to claim 5, wherein the CFTR mutation is G551D, G178R, G551S, S549N, G1349D, R117H, R117C, R347P or R334W.

8. A method according to claim 5, wherein the CFTR mutation is R117H.

9. A method according to claim 4, wherein the patient is heterozygous with (i) one allele displaying a class III or class IV CFTR mutation and (ii) the other allele displaying a class II CFTR mutation.

10. A method according to claim 4, wherein the patient is susceptible to, or suffering from, diarrhoea.

11. A method according to claim 10, wherein the patient is suffering from ulcerative colitis, Crohn's disease, microscopic colitis, celiac disease, irritable bowel syndrome, bile acid malabsorption, or diverticulitis.

12. A product comprising (a) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof, and (b) a CFTR potentiator or a CFTR corrector for simultaneous, separate or sequential use in treating or preventing cystic fibrosis in a patient.

13. A method for treating or preventing cystic fibrosis in a patient, the method comprising administering to the patient (a) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof simultaneously, separately or sequentially in combination with (b) a CFTR potentiator or a CFTR corrector.

14. A method for treating or preventing cystic fibrosis in a patient, the method comprising administering to the patient (b) a CFTR potentiator or a CFTR corrector simultaneously, separately or sequentially in combination with (a) 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one or a pharmaceutically acceptable acid addition salt thereof.

* * * * *